(12) United States Patent
MacLean

(10) Patent No.: US 7,670,319 B1
(45) Date of Patent: Mar. 2, 2010

(54) SAFETY DEVICE FOR USE WITH A VIAL

(75) Inventor: David R. MacLean, Chesterfield, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 945 days.

(21) Appl. No.: 09/550,049

(22) Filed: Apr. 14, 2000

(51) Int. Cl.
*A61M 5/32* (2006.01)

(52) U.S. Cl. .................. 604/192; 604/263; 604/198; 604/187

(58) Field of Classification Search ......... 604/192–198, 604/181, 240–3, 263, 110, 187, 272; 128/763
See application file for complete search history.

(56) References Cited

U.S. PATENT DOCUMENTS

| | | | | |
|---|---|---|---|---|
| 4,659,330 A | * | 4/1987 | Nelson et al. | 604/192 |
| 5,002,536 A | * | 3/1991 | Thompson et al. | 604/192 |
| 5,135,509 A | * | 8/1992 | Olliffe | 604/192 |
| 5,139,489 A | * | 8/1992 | Hollister | 604/192 |
| 5,649,622 A | * | 7/1997 | Hollister | 206/365 |
| 5,662,617 A | | 9/1997 | Odell | |
| 5,669,889 A | * | 9/1997 | Gyure et al. | 604/263 |
| 5,681,295 A | | 10/1997 | Gyure et al. | |
| 5,733,265 A | * | 3/1998 | Bachman et al. | 604/263 |
| 5,891,103 A | | 4/1999 | Burns | |
| 6,524,281 B1 | * | 2/2003 | Hudon | 604/263 |
| 6,575,941 B1 | * | 6/2003 | Mumford | 604/192 |

FOREIGN PATENT DOCUMENTS

| | | |
|---|---|---|
| WO | 93/16745 | 9/1993 |
| WO | 00/41749 | 7/2000 |

\* cited by examiner

*Primary Examiner*—Kevin C Sirmons
*Assistant Examiner*—Phillip Gray
(74) *Attorney, Agent, or Firm*—Louis Woo

(57) ABSTRACT

A safety device to be used with a vial, or capsule, has a collar dimensioned to slidably fit about the body of the vial. Extending from the collar is a neck member that has connected to its other end a housing pivotable to a position along the longitudinal axis of the vial. A latch member having a lip is integrated to the neck member and extends out from the neck member in a direction towards the center of the collar. Neck member is fabricated to have an elastic characteristic so that if it is not biased by any external force, it will return to its original position. As the collar of the safety device is moved along the body of the vial, neck member is biased away from the vial as the latch member maintains contact along the outer surface of the vial, and then the outer surface of the hub formed at the top end of the vial. Once the collar of the safety device is moved to a position adjacent the hub, given the configuration of the neck member forms a space between the top of the collar and the lip of the latch member, the hub of the vial would fit within the space thus formed, as neck member snaps back to its original position. At which time the lip of latch member latches onto a shoulder portion of the hub. Once latched onto the hub, the latch member would prevent the safety device from being removed from the vial. Instead of the neck member, another embodiment of the inventive safety device has extending from the collar a rigid support frame and an elongate elastic latch member.

12 Claims, 4 Drawing Sheets

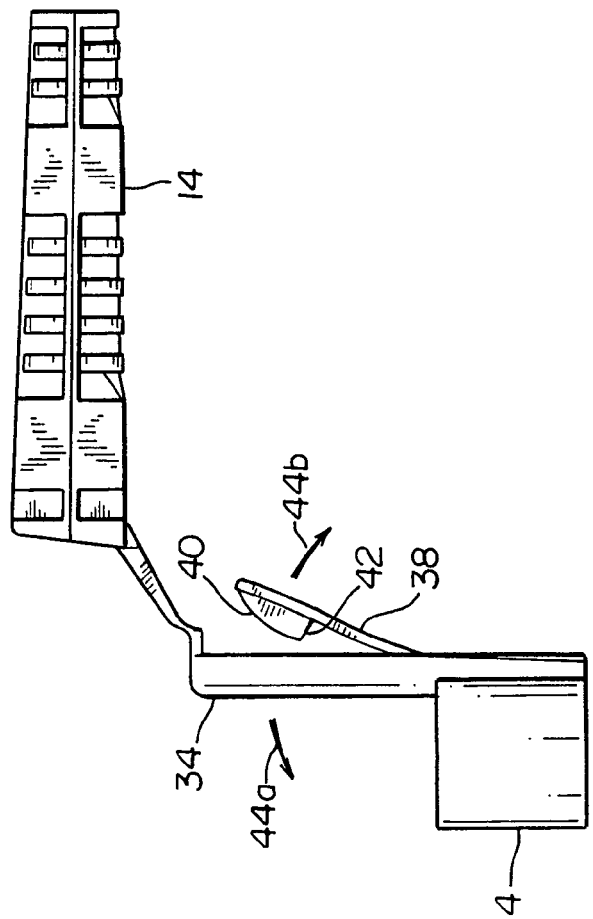
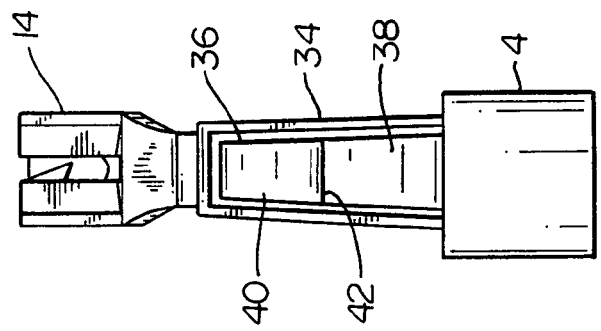

SAFETY DEVICE FOR USE WITH A VIAL

RELATED APPLICATIONS

This application is related to patent application Ser. No. 09/227,819 filed Jan. 11, 1999, now U.S. Pat. No. 6,334,857 entitled "Needle Protection Apparatus Used With A Vial", assigned to the same assignee as the instant invention. This application is furthermore related to U.S. Pat. No. 6,524,281 entitled "Needle Protection Device For Use With A Vial", assigned to the same assignee as the instant application. The disclosures of the '857 and '281 patents are incorporated by reference to the instant application.

FIELD OF THE INVENTION

The present invention relates to needle protection devices, and more particularly to a safety device that is securely coupled to a vial so that, once the needle extending from the vial is used, the housing of the safety device can be pivoted to enclose the contaminated needle so as to prevent the contaminated needle from being further exposed to the environment.

BACKGROUND OF THE INVENTION

Needle protection devices for use with a vial that contains medicament to be used with applicators such as Tubex and Carpuject holder applicators are disclosed in the aforenoted '819 application (the '857 patent). One of the related devices disclosed in the '819 application has a collar that slidably fits over the hub of a vial and is secured thereto by means of a number of extending fingers. Another of the '819 devices has an open collar that mounts about the vial. A pair of interlocking extensions from the collar coact to secure the collar about the vial. Although worked well, these devices fail to take full advantages of the structure of the vial itself and the interaction between the vial and the holder applicators, in order to be securely coupled to the vial. The '089 co-pending application discloses the use of the hub of the vial as a means for securing the collar fitted about the vial. The present invention discloses yet another needle safety device that takes into consideration the inherent characteristic of the vial, and the relationship between the vial and its hub, for securing itself to the vial.

SUMMARY OF THE PRESENT INVENTION

The present invention safety device has a collar that has a dimension that allows it to matingly fit about the body of a vial or capsule that contains a fluid such as medicament. Extending from the collar is a neck member that is dimensioned to have a predetermined length. Flexibly integrated to the other end of the neck member is a housing that, once the collar is fitted appropriately to the vial, could be pivoted to a position in substantial alignment along the longitudinal axis of the vial to envelop the needle extending from a hub formed at the end of the vial.

Taking into consideration the inherent characteristics of a typical medicament container vial, the neck member of the instant invention safety device is configured to have extending therefrom a latch member that has a lip which, after the collar is fitted about the body of the vial and moved along the length of the vial to adjacent the hub of the vial, latches on the top, or a shoulder, of the hub so as to fixedly attach the instant invention safety device to the vial.

This is possible because the safety device is made of a plastic material that provides a given elastic or flexible characteristics to the neck member to enable it to be in guiding contact with the sidewall of the hub as the collar is being pushed to the position adjacent the hub. The elastic characteristics of the neck member enables the neck member to return to its original position, with respect to the collar, once the collar is positioned to the predetermined location adjacent the hub, so that the latch member that extends from the neck member would snappingly latch onto the top portion, i.e., the shoulder of the hub, at that point. Once thus secured, to prevent a contaminated needle from being further exposed to the environment, the housing that is flexibly connected to the neck member is pivoted towards the contaminated needle until the latter is covered. A locking mechanism integrated to the housing would then fixedly hold the needle in place.

Instead of having a flexible neck member, a second embodiment of the instant invention utilizes a substantially rigid support frame that extends from the collar of the device. Also extending from the collar within the confines of the support frame is a flexible latch member that snappingly latches onto the hub of the vial when the collar is moved to the appropriate location along the vial adjacent the hub. The rigid support frame allows for greater tolerances in fitting the collar to different vials.

Both embodiments of the instant invention discussed above are fitted to holder applicators such as for example a Carpujet applicator. Once firmly seated within the cavity of the holder, a mechanism integral to the applicator is actuated to apply a biasing force to the vial so as to secure the vial within the holder, and thereby further securing the collar to the vial.

It is therefore an objective of the present invention to provide a needle protection device that can securely fit to a conventional vial or capsule.

It is yet another objective of the present invention to provide a needle protection device to a vial that allows the vial to be readily used with a conventional holder applicator.

It is moreover an objective of the instant invention to provide a needle safety device that could not readily be removed from the vial once it is fitted to the vial.

BRIEF DESCRIPTION OF THE FIGURES

The above-mentioned objectives and advantages of the present invention will become apparent and the invention itself will be best understood with reference to the following description of embodiments of the present invention taken in conjunction with the accompanying drawings, wherein:

FIG. 9 is a front view of another embodiment of the present invention safety device;

FIG. 10 is a side view of the safety device of FIG. 9; and

DETAILED DESCRIPTION OF THE INVENTION

Figure 1:
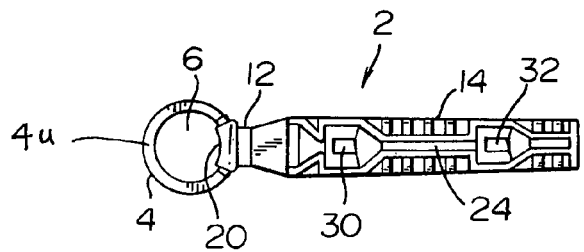
FIG. 1 is a top view of the safety device of the instant invention.
Figure 2:
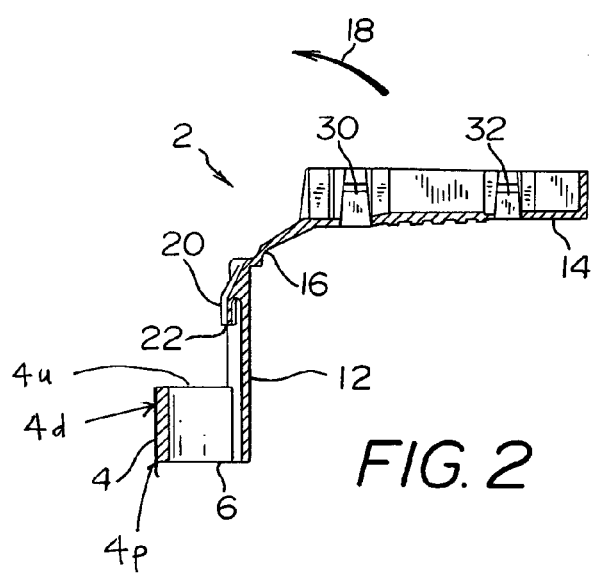
FIG. 2 is a cut-away cross-sectional view of the FIG. 1 device.
Figure 8:
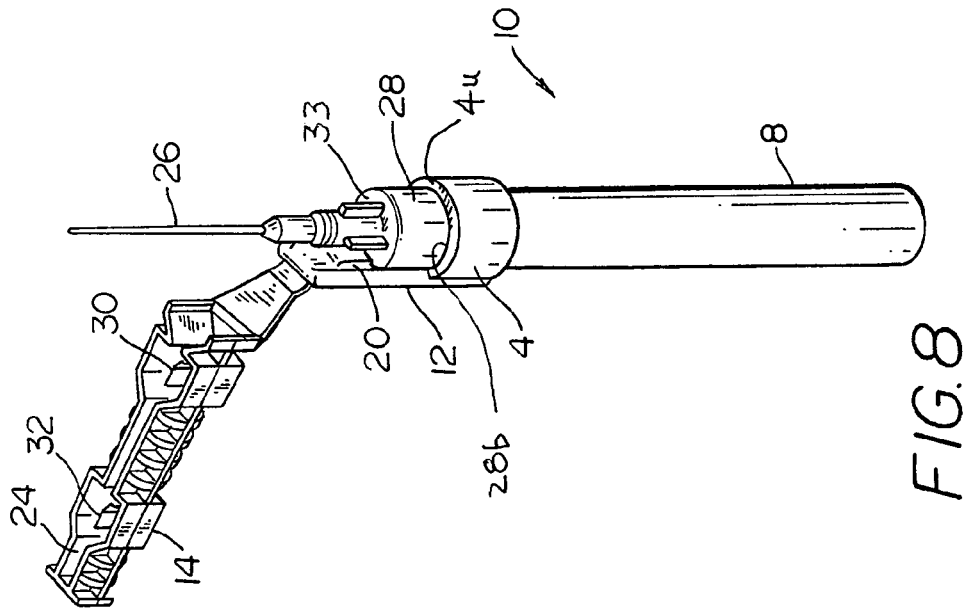
FIG. 8 is a perspective view of a vial having fitted thereto the safety device of the instant invention.
Figure 7:
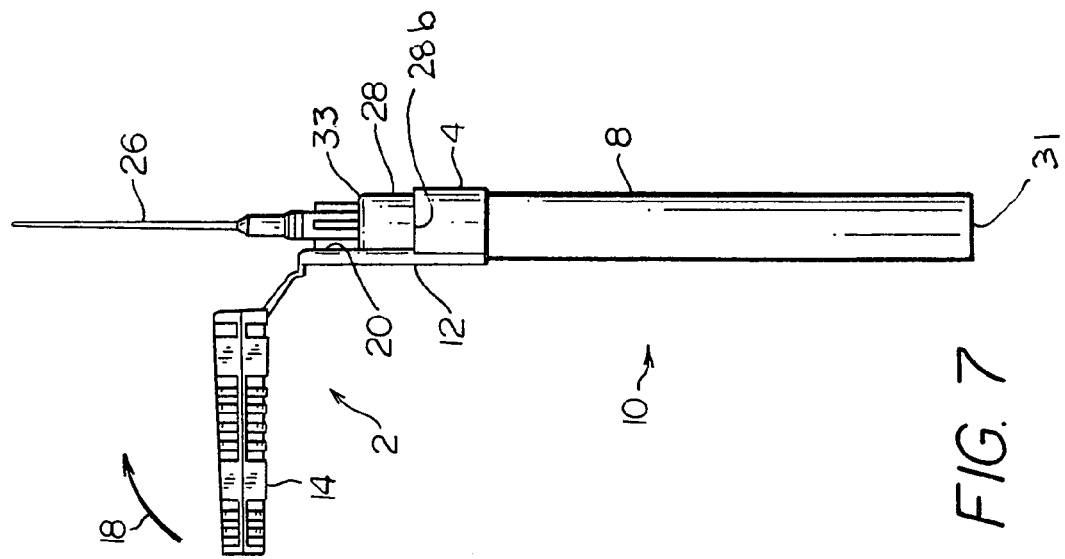
FIG. 7 is a side view of a vial having fitted thereto the safety device of the instant invention.

With reference to FIGS. 1 to 4, safety device 2 of the instant invention is shown to include a collar 4 that forms an opening 6 dimensioned to matingly fit about the body of a vial or capsule, such as for example body 8 of vial 10 as shown in FIGS. 7 and 8. Collar 4 has a distal end 4d and a proximal end 4p. Integrally extending from collar 4 is a neck member 12. Flexibly or hingedly connected to the end of neck member 12 away from collar 4 is a housing or a sheath 14. Housing 14 is integrally connected to neck member 12 by means of a living hinge 16, as best shown in FIG. 5. Thus, as shown in FIG. 2, housing 14 is pivotable about hinge 16 along the direction indicated by directional arrow 18.

As best shown in FIG. 5, a latch member 20 is integrally formed at neck member 12 so as to extend in a direction towards the center of collar 6. As shown, latch member 20 has a lip 22 at its lowermost extension. Further shown in FIGS. 1 and 4, latch member 20 is configured to have a semi-circular outer surface, so as to better form fit with the outer circumferential surfaces of body 8 of vial 10 and the hub formed at the top end of vial 8.

Neck member 12, molded or fabricated to have an elastic characteristic, is a flexible upright that extends from collar 12 along a predetermined axis substantially parallel to the longitudinal axis of body 8. Unless biased by an external force, neck member 12 would maintain its molded position. Thus, were neck member 12 biased by an external force, once that force is removed, being flexible, it will spring back to its predisposed original position.

Figure 4:
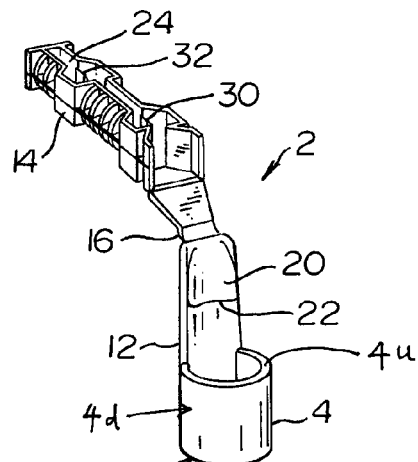
FIG. 4 is a perspective view of the safety device of the instant invention.
Figure 5:
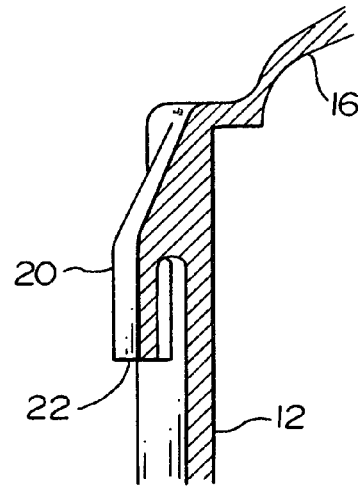
FIG. 5 is an enlarged view of the latch member shown cross-sectionally with respect to the neck member of the safety device of the instant invention.
Figure 3:
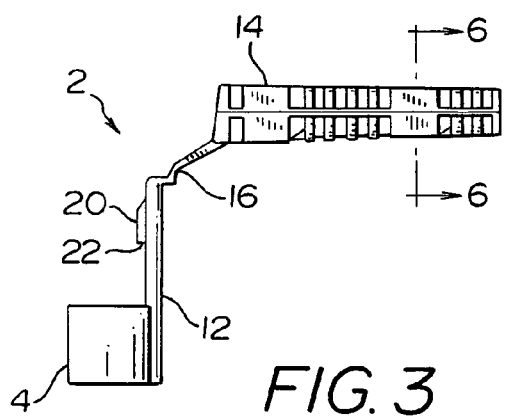
FIG. 3 is a side view of the FIG. 1 device.
Figure 6:
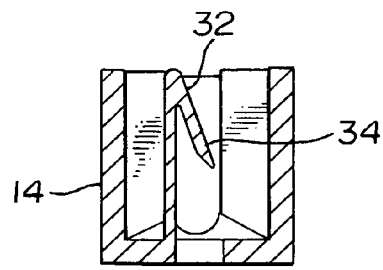
FIG. 6 is a cross-sectional view of A-A as shown in FIG. 3.

Further with respect to FIGS. 1 and 4, housing 14 is shown to have a slot 24 that extends substantially longitudinally along the length thereof so that, as it is pivoted along direction 18, slot 24 allows a needle such as 26 extending from hub 28 of vial 10 to pass therethrough. See FIG. 7. Integrally formed in housing 14 are a number of locking means such as for example hooks 30 and 32. Each of the hooks, for example 32 as shown in FIG. 6, includes a biasing and gripping tip 34.

The interrelationship between safety device 2 and vial 10, in particular the mating of device 2 to vial 10, is best illustrated in FIGS. 7 and 8. To get to its final position with respect to vial body 8 as shown in FIGS. 7 and 8, collar 4 of device 2 is first placed at end 31, i.e., the glass end, of vial body 8. Collar 4 is then matingly fitted to vial body 8 and matably slid along body 8 towards hub 28 until it is moved to a position adjacent the base of hub 28 as shown in FIGS. 7 and 8 where bottom surface 28b at the base of hub 28 abuts against upper surface 4u of collar 4. Given that device 2 is made of a plastic material and neck member 12 is formulated to have an elastic characteristic that makes it flexible, as latch member 20 comes into contact with body 8, neck member 12 is flexibly pushed away from body 8. As collar 4 is moved towards hub 28, latch member 20 maintains its guided contact with body 8. When latch member 20 comes into contact with the side surface of hub 28, it causes neck member 12 to flex even further away, so as to allow collar 4 to continually be pushed towards hub 28.

At the location as shown in FIGS. 7 and 8 where collar 4 is positioned adjacent the base of hub 28 whereby bottom surface 28b of hub 28 abuts against upper surface 4u of collar 4, given its elastic property, with lip 22 of latch member 20 being positioned at shoulder 33 of hub 28, neck member 12 would snappily flex back to its original position to thereby cause latch member 20 to coact with shoulder 33 of hub 28 to thereby latch lip 22 onto shoulder 33. As a consequence, collar 4 is fixedly coupled to vial body 8 and hub 28 thereof due to the respective coacting relationships between latch member 20 with shoulder 30 and between the base of hub 28 and the distal end of collar 4. And absent a concerted effort by the user to push neck member 12 away from hub 28, collar 4 could not be removed from body 8 as it is held in a fixed longitudinal relationship relative to hub 28.

Note that although fixedly coupled to body 8 and hub 28, collar 4 and therefore device 2 nonetheless is rotatable about body 8. Note further that neck member 12 is fabricated to have a given length so that there is sufficient distance along neck member 12 separating latch member 20 from collar 4 to form a space that allows hub 28 to comfortably fit therein once neck member 12 snaps back to its original position and latch member 20 latches onto the shoulder of hub 28.

Once collar 4 is positioned as shown in FIGS. 7 and 8, to prevent a contaminated needle such as for example needle 26 from being further exposed to the environment, the user only needs to pivot housing 14 in the direction as shown by directional arrow 18. Once housing 14 is moved to a position in substantial alignment along the longitudinal axis of body 8 of vial 10, the tips 35 of hooks 30 and 35 would first bias needle 26 and then lockingly grip the same, to thereby fixedly retain needle 26 within housing 14.

Once housing 14 is thus fixedly positioned relative to needle 26, safety device 2 becomes permanently fixed to vial 10, as neck member 12 could no longer be pushed away from hub 28, concerted efforts by the user notwithstanding. This is because needle 26 acts to anchor safety device 2 to body 8 and hub 28 to thereby prevent neck member 12 from being further flexed.

Another embodiment of the present invention is shown in FIGS. 9 and 10. The elements in FIGS. 9 and 10 that are the same as those shown in FIGS. 1 to 8 are labeled the same. Instead of neck member 12, the embodiment shown in FIGS. 9 and 10 has extending from collar 4 a support frame member 34. Instead of being solid as the case of neck member 12, support frame 34 is a support that frames an opening 36, and is constructed as a substantially rigid member.

Also extending from collar 4 is an elongated member 38 that includes a latch member 40 having a lip portion 42. As best shown in FIG. 10, elongate member 38 is configured to be flexible so that it could flex in both directions, as indicated by arrows 44a and 44b in a somewhat exaggerated fashion, relative to support frame 34. By providing a rigid support frame member 34 and a flexible elongate flexible latch member 40, the embodiment of the safety device shown in FIGS. 9 and 10 is more tolerance adaptable for vials that may have hubs of different sizes.

Although shown to be extending in an upright fashion from collar 4, given that it is a rigid member, in practice, support frame 34 may actually be extending from collar 4 in a somewhat offset manner so as to enable collar 4 to be readily slidable over body 8 of vial 10. And as far as elongate member 38 is flexible and is molded or formed to naturally extend in an upright fashion relative to collar 4, latch member 40 would continue to be flexibly guided by the side surface of body 8, and then hub 28, as collar 4 is matingly slid longitudinally along body 8 of vial 10. As was with the previous embodiment, once collar 4 is positioned properly adjacent hub 28 to abut against lower surface 28b of hub 28, elongate member 38 will snappingly return to its original shape so that lip 42 of latch member 40 would coact with shoulder 32 of hub 28 to thereby latch onto hub 28 to fixedly retain collar 4 relative to hub 28.

Figure 11:
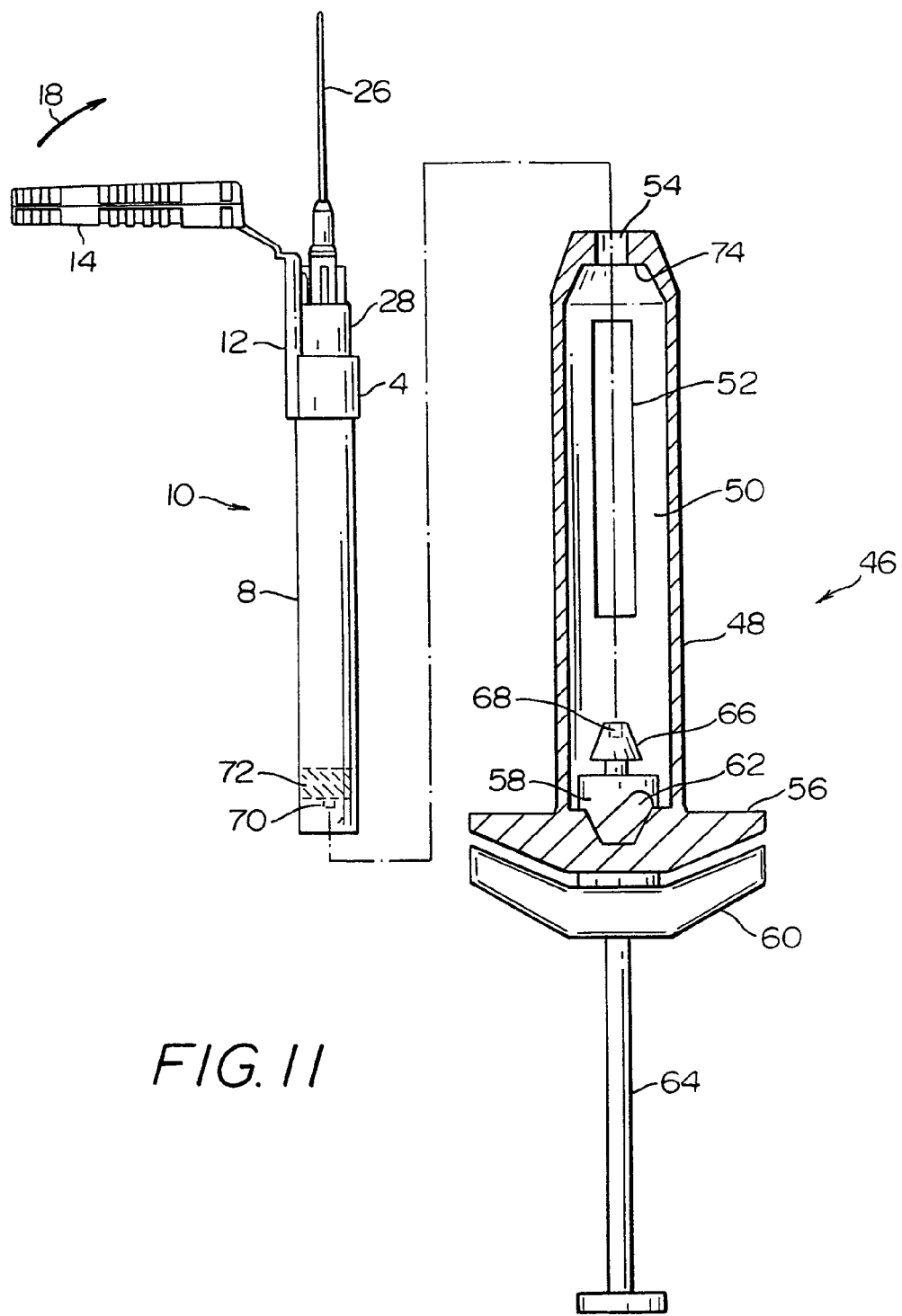
FIG. 11 is an illustration of a holder applicator and how it relates to a vial having fitted thereon the safety device of the instant invention.

FIG. 11 illustrates the interrelationship of a vial fitted with the safety device of the instant invention and a holder applicator such as for example a Carpuject applicator. As shown, holder 46 has an elongated housing 48 having a cavity 50. The side of housing 48 facing the reader is opened to the environment and an aperture 52 is formed at its opposite side. At the tip of housing 48 there is a an opening or channel 54. At its other end housing 48 is mounted to a finger grip base 56. A bore (not shown) extends through base 56.

Inserted through the bore of base 56 is a cylinder 58 that extends from another base 60 that has a shape substantially similar to that of base 56. Cylinder 58 has a groove 62 that mates with a bump protrusion (not shown) formed at the inner surface of the bore of base 56 for guiding cylinder 58 when it is turned synchronously with the rotation of base 60. When cylinder 58 is turned to either of its extreme end positions, absent an external force, it is locked into position by the bump protrusion.

Another bore, not shown, extends along the length of cylinder 58. A rod 64, freely coupled to base 60 through the bore of cylinder 58, is movable along the length of holder 48. Rod 64 has a head 66 with a threaded internal portion 68 for mating with a screw 70 fitted to an elastic gasket 72 slidably fitted within body 8 of vial 10.

In operation, once fitted with collar 4, body 8 of vial 10 is placed into cavity 50 of holder 48. Prior to positioning vial 8 in cavity 50, rod 64 is pulled to its furthest removed position, and base 60 is turned in a counterclockwise (or clockwise) release direction so as to lower cylinder 58 to its lowermost position.

Once vial 8 is fitted into cavity 50, rod 64 is moved to mate internal threaded cavity 68 with threaded screw 70 of elastic gasket 72. Once that is done, base 60 is turned in a clockwise (or counterclockwise) locking direction to apply a biasing force against body 8 of vial 10. Given that vial 10 is positioned in cavity 50 of holder 48 with hub 28 being biased against a front end 74 of holder 48 (with needle 26 passing through channel 54), by turning base 60 to its extreme locking position, vial 10, with collar 4 appropriately fitted thereto, is fixedly retained within holder 48.

To eject whatever fluid is stored in body 8 of vial 10, the user would push rod 64 in a direction towards front end 74, to thereby push elastic gasket 72 in body 8 of vial 10 towards hub 28. After the medicament stored in body 8 has been ejected and needle 26 withdrawn from the patient, to prevent contaminated needle 26 from being exposed to the environment, housing 14 is pivoted along direction 18 to envelop needle 26, which is then held in place by locking means 32 of housing 14.

To discard the vial, the reverse process with respect to the actuation of base 60 and rod 64 as described above takes place. That is, base 60 is turned to its extreme release position to lower cylinder 58 to its lowermost position. Rod 64 is then turned to release head 66 from screw 70. Upon further withdrawal of rod 64 from gasket 72, vial 10 could then be lifted out of cavity 50 of housing 48 and discarded in an appropriate manner.

It should be appreciated that the present invention is subject to many variations, modifications, and changes in detail. For example, even though the holder applicator shown in FIG. 11 has been described as being used to inject a patient with a medicament stored in the vial, it should be appreciated that an empty vial could be used to withdraw bodily fluids from a patient. Moreover, although the safety device of the instant invention is disclosed above as being matably fitted about the vial at its glass end first, it should be appreciated that the collar of the inventive safety device could be dimensioned such that it could be fitted to the body of the vial via the end at which the needle extends from the hub. To accomplish this, a biasing means, such as for example an elastic ring with a cross-sectional cut-out, could be fitted to the inside of collar 4 so that the inside diameter of collar 4 could vary, thereby enabling collar 4 to be fitted about the body of the vial from the needle end of the vial. Accordingly, all matters described throughout this specification and shown in the accompanying drawings should be interpreted as illustrative only and not in a limiting sense. It is therefore intended that this invention be limited only by the spirit and scope of the hereto appended claims.

The invention claimed is:

1. Safety device usable with a vial, said vial having mounted to one of its ends a hub from which a needle extends, said hub having a shoulder and a base, said safety device comprising:
    a collar slidably matable about said vial, said collar having a distal end;
    a neck member extending from the distal end of said collar;
    a housing pivotably connected to end of said neck member away from said collar; and
    a latch member extending from said neck member in a direction towards center of said collar, said latch member coacting with the shoulder of said hub and the distal end of said collar coacting with the base of said hub to prevent said collar from being removed from said vial once said collar has been mated about said vial and the distal end of said collar is positioned adjacent said hub.

2. Safety device of claim 1, wherein said latch member is integrated to said neck member; and
    wherein said neck member is flexible with respect to said collar so that said latch member is guided along the side of said hub as said collar is moved towards said hub, said latch member latching onto a shoulder of said hub when said collar is moved adjacent to said hub.

3. Safety device of claim 1, wherein said latch member is integrated to a location along said neck member so as to effect a space between said latch member and said collar along said neck member whereinto said hub matingly fits after said collar is moved adjacent to said hub and said latch member is moved into position to latch onto a shoulder of said hub.

4. Safety device of claim 1, wherein said neck member is flexible with respect to said collar so that once said collar is moved to a given position relative to said hub, said neck member flexes to a position to enable said latch member to latch onto a shoulder of said hub; and
    wherein said housing comprises a slot wherethrough said needle passes when said housing is pivoted to a position in substantial alignment with the longitudinal axis of said vial, said housing further including at least one locking means for fixedly maintaining said needle relative to said housing once said housing is pivoted to said alignment position;
    wherein once fixed relative to each other, said needle and said housing interact to prevent said neck member from flexing away from said hub and said latch member from being disengaged from said shoulder of said hub.

5. Safety device of claim 4, wherein said locking means comprises a hook integrated to interior of said housing for holding said needle fixed relative to said housing once said housing is pivoted to said alignment position and said needle biases and then is held by said hook.

6. Safety device of claim 1, wherein said neck member comprises a flexible upright extending from said collar, and wherein said latch member comprises a lip extending at its tip, said lip latching onto a shoulder of said hub when said collar is moved adjacent to said hub.

7. Safety device, comprising:
   a collar;
   a neck extending from said collar;
   a housing pivotably connected to the end of said neck away from said collar; and
   a latch member extending from said neck in a direction towards the center of said collar;
   wherein when said collar is placed about a vial and moved toward a hub of said vial until adjacent to one end of said hub, said latch member is latched onto another end of said hub.

8. Safety device of claim 7, wherein said latch member is integrated to said neck and flexible relative to said collar.

9. Safety device of claim 7, wherein said housing comprises at least one integral hook for lockingly gripping a needle extending from said hub when said housing is pivoted to a position in alignment along longitudinal axis of said vial.

10. Safety device, comprising: a collar, a flexible neck extending from said collar, a housing pivotably connected to the end of said neck away from said collar, and a latch member extending from said neck in a direction towards the center of said collar, said latch member continuously biases against body of a vial when said collar is placed about said vial and moved toward one end of a hub of said vial, said latch member further biases against said hub as said collar is moved further toward said one end of said hub, said latch member latching onto another end of said hub when said collar is moved adjacent to said one end of said hub.

11. Safety device of claim 10, wherein said latch member is integrated to said neck and flexible relative to said collar.

12. Safety device of claim 10, wherein said housing comprises at least one integral hook for lockingly gripping a needle extending from said hub when said housing is pivoted to a position in alignment along longitudinal axis of said vial.

* * * * *